United States Patent [19]

Metivier et al.

[11] 4,173,709
[45] Nov. 6, 1979

[54] PROCESS FOR THE PREPARATION OF DEXTROROTATORY 2-PHENOXYPROPIONIC ACID DERIVATIVES

[75] Inventors: Jean Metivier; Michel Sauli, both of Paris, France

[73] Assignee: Rhone-Poulenc S.A., Paris, France

[21] Appl. No.: 766,667

[22] Filed: Feb. 8, 1977

Related U.S. Application Data

[63] Continuation-in-part of Ser. No. 746,166, Nov. 30, 1977, abandoned, which is a continuation of Ser. No. 497,461, Aug. 14, 1974, abandoned, which is a continuation of Ser. No. 337,006, Mar. 1, 1973, abandoned, which is a continuation-in-part of Ser. No. 336,832, Feb. 28, 1973, abandoned, which is a continuation of Ser. No. 601,874, Dec. 15, 1966, abandoned.

[30] Foreign Application Priority Data

Dec. 17, 1965 [FR] France ..................... 65.42858

[51] Int. Cl.$^2$ ............................................. C07C 59/26
[52] U.S. Cl. ........................................ 562/471; 562/472
[58] Field of Search .................. 260/521 R, 521 H; 562/471, 472

[56] References Cited

U.S. PATENT DOCUMENTS

| | | | |
|---|---|---|---|
| 2,805,251 | 9/1957 | Marshall et al. | 260/521 H |
| 2,830,083 | 4/1958 | Gilbert et al. | 260/521 H |
| 3,007,962 | 11/1961 | Metivier et al. | 260/521 H |

FOREIGN PATENT DOCUMENTS

| | | | |
|---|---|---|---|
| 571461 | 3/1959 | Canada | 260/521 R |
| 1479271 | 5/1967 | France | 260/521 H |

OTHER PUBLICATIONS

Eliel, Stereochemistry of Carbon Compounds, pp. 47–50, (1962).
Finar, "Org. Chem.," pp. 39–39 & 72–73, (1959).
Eliel–"Stereochemistry of Carlson Compounds," (1962), pp. 114–119.
Gould, "Mech. & Structure in Org. Chem.," pp. 270–271, (1959), Holt et al., (N.Y.).
Fredga et al., (Arkiv fur Kemi), Band 4, Nr 20, pp. 325–330, (1951).
Fredga et al., (Arkiv fur Kemi), Band 3, Nr 47, pp. 429–436, (1951).
Caserio, "Basic Principles of Organic Chemistry," (1964), pp. 295–297 & 300–305.

Primary Examiner—Jane S. Myers
Attorney, Agent, or Firm—Stevens, Davis, Miller & Mosher

[57] ABSTRACT

Dextrorotatory 2-phenoxypropionic acids are made by heating an alkali metal salt of dextrorotatory 2-chloropropionic acid with an alkali metal phenate in an inert organic solvent of high boiling point under reflux.

10 Claims, No Drawings

PROCESS FOR THE PREPARATION OF DEXTROROTATORY 2-PHENOXYPROPIONIC ACID DERIVATIVES

This application is a continuation-in-part of our co-pending application Ser. No. 746,166, filed Nov. 30, 1976, now abandoned, which was a continuation of application Ser. No. 497,461, filed Aug. 14, 1974, now abandoned, which was a continuation of application Ser. No. 337,006 filed Mar. 1, 1973 and now abandoned which was a continuation-in-part of application Ser. No. 336,832 filed Feb. 28, 1973 and now abandoned which was a continuation of application Ser. No. 601,874 filed Dec. 15, 1966, and now abandoned.

This invention relates to a new process for the preparation of the dextrorotatory 2-phenoxypropionic acids of the general formula:

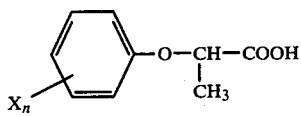

in which the symbol X represents a halogen (preferably chlorine) atom or a methyl group and n is zero or an integer from 1 to 5. When n is an integer from 2 to 5, the substituents present on the benzene ring may be the same or different. It is believed that these dextrorotatory acids have the D configuration.

The herbicidal or phytohormonal properties of racemic propionic acid derivatives conforming to the formula I, such as 2-(4-chloro-2-methylphenoxy)propionic acid or CMPP:

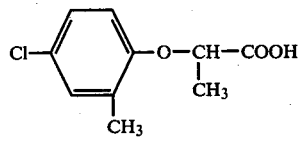

[G. B. Lush, Ang. Chem 70, 112 (1958)], and 2-(2,4-dichlorophenoxy)propionic and 2-(2,4,5-trichlorophenoxy)propionic acids, are known.

It is also known [K. V. Thimann, Plant Growth Substances, p. 21 (1951)] that 2-(2,4-dichlorophenoxy)propionic acid which is dextrorotatory in acetone, ethanol or chloroform, possesses a phytohormonal activity twice as great as that of the racemic acid. It was therefore of interest to obtain the dextrorotatory optical isomers of the above-mentioned propionic acid derivatives.

Hitherto, these optical isomers have been obtained by resolution of the racemic acids [see S. T. Collins and F. E. Smith, J. Sci, Food Agr. 3, 248 (1952) for 2-(2,4-dichlorophenoxy)propionic acid; M. S. Smith, R. L. Wain and F. Wightman, Ann. Appl. Biol. 39, 295 (1952) for 2-(2,4,5-trichlorophenoxy)propionic acid, and M. Matell, Arkiv fur Kemi 6, 365 (1953) for 2-(4-chloro-2-methylphenoxy)propionic acid]. The disadvantage of this method resides first of all in its technical complexity, but also in the fact that, in addition to the biologically active isomer, there is obtained the same quantity of an isomer which is weakly active biologically and therefore useless.

It has now been found, and this forms the subject of the present invention, that 2-phenoxypropionic acids of formula I dextrorotatory in acetone, ethanol and chloroform can be obtained directly by the process which comprises reacting an alkali metal salt of 2-chloropropionic acid of the formula:

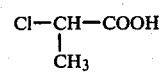

[sodium salt $[\alpha]_D^{22} = +4°$ (c=10, water)], optionally prepared in situ, with an alkali metal (preferably sodium) derivative of a phenol of the general formula:

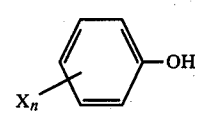

in which X and n are as hereinbefore defined, and treating with an acid the resultant alkali metal salt of the said 2-phenoxypropionic acid.

The reaction is effected in an inert organic solvent of high boiling point such as an aromatic hydrocarbon (for example toluene, b.p. about 111° C., or xylene, b.p. about 144° C.) or a chlorinated hydrocarbon of high boiling point (for example perchloroethylene, b.p. 121° C.) and advantageously at the boiling temperature of the said solvent, i.e. at a temperature at least as high as the boiling point of the simplest inert aromatic hydrocarbon which is 80° C., the boiling point of benzene.

This reaction to give the dextrorotatory 2-phenoxypropionic acids is surprising because, when the reaction is carried out with methyl 2-chloropropionate $[[\alpha]_D^{22} = -27.8°$ (without solvent)] and the resulting product is hydrolysed, there is obtained not an optically active 2-phenoxypropionic acid but the corresponding racemate.

The alkali metal (preferably sodium) salt of 2-chloropropionic acid of formula III may be prepared in situ from an ester of 2-chloropropionic acid [preferably the methyl ester, $[\alpha]_D^{22} = -27.8°$ (without solvent)] by the action of a base (more particularly sodium hydroxide) at a temperature between 5° and 35° C., but, as has already been emphasised, it is important that the hydrolysis of the propionic ester to the alkali metal salt of the acid is effected before the reaction with the phenol derivative of formula IV.

The preferred method according to the invention therefore involves the addition in the cold of an ester of 2-chloropropionic acid to a solution of a phenol of formula IV in an inert organic solvent such as toluene in the presence of an inorganic base such as sodium hydroxide. After agitation for 2 to 4 hours at a temperature between 10° and 35° C., the reaction mixture is heated with reflux of the solvent for 1 to 2 hours. There is thus obtained an alkali metal salt of the desired dextrorotatory 2-phenoxypropionic acid. On acidification of the reaction product, the dextrorotatory 2-phenoxypropionic acid precipitates.

The following Examples illustrate the invention.

EXAMPLE 1

Methyl 2-chloropropionate $[[\alpha]_D^{22} = -27.8°$ (without solvent)] (245 g.) is added over a period of 10 minutes to a solution of o-cresol (216 g.) and sodium hydroxide flakes (164.8 g.) in toluene (1000 cc.) cooled to 15° C., the temperature being maintained between 15° and 20° C. The mixture is stirred for 3 hours at ambient temperature. The reaction mixture is then heated to the reflux temperature of the solvent and this heating is continued for 1 hour 30 minutes. After cooling, distilled water (750 cc.) is added and the aqueous layer is decanted and neutralised by the addition of hydrochloric acid (d=1.19; 80 cc.). Methylene chloride (2×250 cc.) is added, and the aqueous layer is again decanted and is poured into crushed ice (500 g.) with stirring.

The mixture is acidified by the addition of hydrochloric acid (d=1.19; 200 cc.), and an oily precipitate forms, which is extracted with methylene chloride (750 cc.). The organic layer is decanted and the aqueous layer is washed with methylene chloride (100 cc.). The methylene chloride layers are combined and dried over sodium sulphate. After treatment with decolorising charcoal (10 g.), the mixture is filtered and the solvent is evaporated from the filtrate under reduced pressure (25 mm.Hg). After drying to constant weight under reduced pressure (0.1 mm.Hg), D 2-(2-methylphenoxy)-propionic acid (327 g.), m.p. 66–67° C., is obtained; optical rotation $[\alpha]_D^{22} = +18.3°$ (c=10, CHCl$_3$).

Methyl 2-chloropropionate (b.p. 56–58° C./53 mm.Hg) employed as starting material is obtained by the action of thionyl chloride on D methyl lactate $[[\alpha]_D^{22} = +8.25°$ (without solvent)].

EXAMPLE 2

A 40% W/V sodium hydroxide solution (50 cc.) is added over a period of 20 minutes to a solution of o-cresol (56 g.) in refluxing toluene (300 cc.). Water is removed by azeotropic distillation and then sodium 2-chloropropionate $[[\alpha]_D^{22} = +4°$ (c=10, water)] (68 g.) is added, and the mixture is heated for 5 hours at 80° C. After cooling, the reaction mixture is taken up in water (300 cc.), and the aqueous layer is decanted, extracted with methylene chloride (200 cc.) after neutralisation with concentrated hydrochloric acid (d=1.19; 25 cc.), and then poured into a mixture of hydrochloric acid (d=1.19; 50 cc.) and crushed ice (200 g.). The precipitate is extracted with methylene chloride (450 cc.), and the methylene chloride solution so obtained is concentrated under reduced pressure (25 mm.Hg) after drying over sodium sulphate and purification with decolorising charcoal. There is thus obtained D 2-(2-methylphenoxy)propionic acid (77 g.), m.p. 66°–67° C.; optical rotation $[\alpha]_D^{22} = +18.2°$ (c=10, CHCl$_3$).

Sodium 2-chloropropionate $[[\alpha]_D^{22} = +4°$ (c=10, water)] is obtained by the hydrolysis at 5° C. in ethanol of methyl 2-chloropropionate $[[\alpha]_D^{22} = -27.8°$ (without solvent)].

EXAMPLE 3

Methyl 2-chloropropionate $[[\alpha]_D^{22} = -27.8°$ (without solvent)] (122.5 g.) is added over a period of 15 minutes to a solution of 4-chloro-2-methylphenol (142.5 g.) and sodium hydroxide flakes (82.5 g.) in toluene (700 cc.) cooled to 7° C. The mixture is agitated for 5 hours, the temperature being maintained below 20° C., for 2 hours and then below 30° C., for 3 hours. The reaction mixture is then heated to the reflux temperature of the solvent and heating it continued for 1½ hours.

After cooling, distilled water (300 cc.) is added and the aqueous layer is decanted and neutralised with hydrochloric acid (d=1.19; 20 cc.). After the addition of methylene chloride (2×200 cc.), the aqueous layer is decanted, poured into crushed ice (300 g.) and acidified by the addition of hydrochloric acid (d=1.19; 110 cc.). The white precipitate obtained is extracted with methylene chloride (750 cc.). The organic layer is decanted, dried over sodium sulphate, treated with decolorising charcoal (5 g.), filtered and the solvent evaporated from the filtrate under reduced pressure (25 mm.Hg). After drying to constant weight under reduced pressure (0.1 mm.Hg), D 2-(4-chloro-2-methylphenoxy)-propionic acid (193 g.), m.p. 96° C., is obtained; optical rotation $[\alpha]_D^{22} = +17.7°$ (c=10, CHCl$_3$), $[\alpha]_D^{22} = +29.8°$ (c=1, acetone).

EXAMPLE 4

By proceeding as in Example 1 but starting with 2,4,5-trichlorophenol (16 g.) and methyl 2-chloropropionate $[[\alpha]_d^{22} = -27.8°$ (without solvent)] (10 g.), D 2-(2,4,5-trichlorophenoxy)propionic acid (12 g.), m.p. 143–144° C., is obtained; optical rotation
$[\alpha]_D^{22} = +37°$ (c=2.5, CHCl$_3$)
$[\alpha]_D^{22} = +33.3°$ (c=1, CHCl$_3$)

EXAMPLE 5

By proceeding as in Example 1 but starting with 2,4-dichlorophenol (163 g.) and methyl 2-chloropropionate $[[\alpha]_D^{22} = -27.8°$ (without solvent)] (122.5 g.) D 2-(2,4-dichlorophenoxy)propionic acid (210 g.), m.p. 123°–124° C., is obtained; optical rotation $[\alpha]_D^{20} = +19.3°$ (c=10, (CHCl$_3$).

EXAMPLE 6

Sodium hydroxide flakes (25.2 g.) are added to a solution of 2,4-dichlorophenol (97.8 g.) in refluxing perchloroethylene (500 cc) and water is removed by azeotropic distillation. Sodium 2-chloropropionate $[[\alpha]_D^{22} = +4°$ (c=10, water)] (78.3 g) is then slowly added to the suspension formed in perchloroethylene, while heating it for 3 hours at refluxing temperature and removing the water by azeotropic distillation.

After cooling, the reaction mixture is taken up with water (500 cc) and the aqueous layer is decanted. The organic layer is then washed with water (200 cc) and the two aqueous layers are joined together and extracted with methylene chloride (500 cc) after neutralisation to PH7 with hydrochlorid acid. After decantation, the aqueous layer is discoloured with charcoal, filtrated and then acidified with hydrochlorid acid (aqueous solution at 3.6% w/v) (700 cc).

The precipitate is then filtered, washed in water, agitated with cyclohexane (200 cc), filtrated again and dried under reduced pressure.

D 2-(2,4-dichlorophenoxy)propionic acid (120 g.) m.p. 125° C., is obtained. Optical rotation $[\alpha]_D^{22} = +35.5°$ (c=1, acetone).

Sodium 2-chloropropionate $[[d]_D^{22} = +4°$ (c=10, water)] (78.3 g was obtained by the hydrolysis of methyl 2-chloro propionate $[[\alpha]_D^{22} = -27.8°$ (without solvent)] (73.5 g.), at 7° C. in ethanol (20 cc) by sodium hydroxide (40% w/v solution) (60 cc).

The process of the present invention is of particular interest for the preparation of the dextrorotatory isomers of 2-(4-chloro-2-methylphenoxy)propionic acid, 2-(2,4-dichlorophenoxy)propionic acid, 2-(2,4,5-trichlorophenoxy)propionic acid and 2-(2-methylphenoxy)propionic acid.

We claim:

1. A process for the preparation of a 2-phenoxypropionic acid dextrorotatory in acetone, ethanol and chloroform, of the formula:

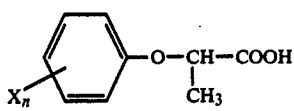

in which the symbol $X_n$ represents o-methyl, 4-chloro-2-methyl, 2,4,5-trichloro-, or 2,4-dichloro-, which comprises heating an alkali metal salt of 2-chloropropionic acid whose sodium salt has an optical rotation $[\alpha]_D^{22} = +4°$ (c=10, water) with an alkali metal derivative of a phenol of the formula:

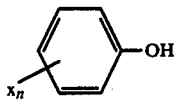

in which the symbol $x_n$ is as hereinbefore defined, in a refluxing inert aromatic hydrocarbon solvent of high boiling point, and treating with an acid the resultant alkali metal salt of the said 2-phenoxypropionic acid.

2. A process for the preparation of a 2-phenoxypropionic acid dextrorotatory in acetone, ethanol and chloroform, of the formula:

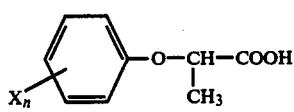

in which the symbol $x_n$ represents o-methyl-, 4-chloro-2-methyl, 2,4,5-trichloro-, or 2,4-dichloro-, which comprises heating an alkali metal salt of 2-chloropropionic acid whose sodium salt has an optical rotation $[\alpha]_D^{22} = +4°$ (c=10, water) with an alkali metal derivative of a phenol of the formula:

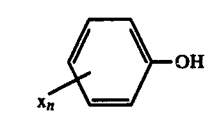

in which the symbol $x_n$ is as hereinbefore defined, in a refluxing inert organic hydrocarbon solvent of high boiling point, and treating with an acid the resultant alkali metal salt of the said 2-phenoxypropionic acid.

3. A process for the preparation of a 2-phenoxypropionic acid dextrorotatory in acetone, ethanol and chloroform, of the formula:

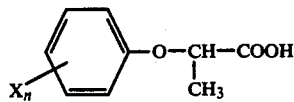

in which the symbol $X_n$ represents o-methyl, 4-chloro-2-methyl, 2,4,5-trichloro-, or 2,4-dichloro-, which comprises heating an alkali metal salt of 2-chloropropionic acid whose sodium salt has an optical rotation $[\alpha]_D^{22} = +4°$ (c=10, water) with an alkali metal derivative of a phenol of the formula:

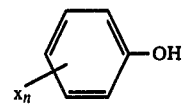

in which the symbol $x_n$ is as hereinbefore defined, in a refluxing inert organic solvent of boiling point at least as high as that of an aromatic hydrocarbon solvent, and treating with an acid the resultant alkali metal salt of the said 2-phenoxypropionic acid.

4. A process for the preparation of a 2-phenoxypropionic acid dextrorotatory in acetone, ethanol and chloroform, of the formula:

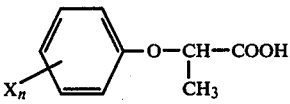

in which the symbol $X_n$ represents o-methyl-, 4-chloro-2-methyl, 2,4,5-trichloro-, or 2,4-dichloro-, which comprises heating an alkali metal salt of 2-chloropropionic acid whose sodium salt has an optical rotation $[\alpha]_D^{22} = +4°$ (c=10, water) with an alkali metal derivative of a phenol of the formula:

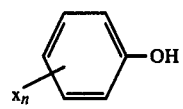

in which the symbol $x_n$ is as hereinbefore defined, in a refluxing inert organic solvent of boiling point from about 111° to 144° C., and treating with an acid the resultant alkali metal salt of the said 2-phenoxypropionic acid.

5. A process according to claim 1 in which the alkali metal salt of 2-chloropropionic acid is prepared in situ by the action of an alkali metal base on an ester of 2-chloropropionic acid at a temperature between 5° and 35° C.

6. A process according to claim 5 in which the alkali metal base is sodium hydroxide.

7. A process according to claim 1 in which the alkali metal salt of 2-chloropropionic acid is prepared in situ by the action of sodium hydroxide on methyl 2-chloropropionate $[[\alpha]_D^{22} = -27.8°$ (without solvent)] at a temperature between 5° and 35° C.

8. A process according to claim 1 in which the alkali metal salt of the dextrorotatory 2-phenoxypropionic acid obtained as reaction product is converted to the corresponding acid by treatment with hydrochloric acid.

9. A process according to claim 1 which comprises adding an ester of 2-chloropropionic acid to a cold solution of a phenol of the formula specified in claim 1 in the inert aromatic hydrocarbon solvent in the presence of sodium hydroxide, agitating the reaction mixture for 2 to 4 hours at a temperature between 10° and 35° C., and then heating it under reflux conditions for 1 to 2 hours, and acidifying the alkali metal salt of the said 2-phenoxypropionic acid so obtained to yield the said 2-phenoxypropionic acid.

10. A process according to claim 1 in which the inert aromatic hydrocarbon solvent is toluene or xylene.

* * * * *